United States Patent [19]
Turanyi et al.

[11] Patent Number: 5,344,460
[45] Date of Patent: Sep. 6, 1994

[54] PROSTHESIS SYSTEM

[75] Inventors: Sandor Turanyi, Red Rock; Robert Jones, Lockhart; John D. Webb, Jr., Round Rock, all of Tex.

[73] Assignee: Encore Orthopedics, Inc., Austin, Tex.

[21] Appl. No.: 969,129

[22] Filed: Oct. 30, 1992

[51] Int. Cl.5 .................. A61F 2/38; A61F 2/30; A61F 2/28
[52] U.S. Cl. ..................... 623/20; 623/18; 623/16
[58] Field of Search ............... 623/20, 18, 16

[56] References Cited

U.S. PATENT DOCUMENTS

| | | | |
|---|---|---|---|
| 3,945,053 | 3/1976 | Hillberry et al. | 623/20 |
| 4,795,468 | 1/1989 | Hodorek | 623/20 X |
| 4,963,152 | 10/1990 | Hoffmann et al. | 623/20 |
| 5,171,276 | 12/1992 | Caspari et al. | 623/20 X |
| 5,201,768 | 4/1993 | Caspari et al. | 623/20 |
| 5,207,711 | 4/1993 | Caspari et al. | 623/20 |

Primary Examiner—Randall L. Green
Assistant Examiner—Dinh Nguyen
Attorney, Agent, or Firm—Winstead Sechrest & Minick

[57] ABSTRACT

A tibial insert and baseplate system is disclosed for a prosthesis. The tibial baseplate is right or left knee specific while the insert is symmetrical about an anterior-posterior centerline and is thus not right or left knee specific. The baseplate has an outer periphery which is asymmetrical to mate exactly with either the left or right tibia but not with both. The upper surface of the baseplate, which also has an asymmetrical periphery, in addition, defines a symmetrical housing within the periphery for the symmetrical insert.

15 Claims, 3 Drawing Sheets

PROSTHESIS SYSTEM

TECHNICAL FIELD OF THE INVENTION

This invention relates to orthopedic prostheses, and more particularly to prostheses utilized in joint replacements.

BACKGROUND OF THE INVENTION

There is a well known fact that the joints of humans as well as animals deteriorate over time. Sometimes deterioration occurs because of disease due to aging and sometimes due to a trauma. The knee joint is perhaps the one joint that has given people the most trouble over the years because of its essential function to the mobility of humans. Thus, quite naturally, a great deal of research has gone into the development of replacement knees. Today, because of this widespread research, a significant portion of our population is again mobile and relatively free of pain. This great step forward in medical research has not been without its difficulties. Primarily because of the tremendous stresses placed on the knee joint, there continues to be a need for improvement to eliminate the last vestiges of pain and suffering.

Prosthetic surgery involving the excision and removal of deteriorated and diseased bone tissue in knee and hip joints has now become quite common. Typically, artificial members of plastic and/or metal compatible with the human body are substituted for the removed natural bone segments and anchored to the remaining bone structure.

The bearing surfaces of the knee joint are especially vulnerable to stress, arthritic and other disease induced deterioration. Prosthetic correction is necessary when the surfaces become so damaged that other less drastic techniques have little or no prospect of success.

In a healthy knee, the lower leg bone, called the tibia, has at its upper end a pair of concave surfaces. These concave surfaces meet with condyles which are formed in the lower end of the femur, which is the upper leg bone. This meeting is protected by the patella (knee cap). Thus, in a knee replacement operation, the upper end of the tibia is removed as is the lower end of the femur, and these bones are replaced with prostheses, which are designed to operate together.

In the past, there have been two major types of knee prostheses: hinged and non-hinged. In one form, the knee was resected and replaced by a metal hinged-type device with deep penetration into the remaining femoral and tibial bone structure by means of flared and thick stems. The range of movement was limited and patients were seldom able to flex the knee beyond 90°. Moreover, implantation required the removal of a significant amount of the bone with a shortening of the limb if for any reason the prosthesis was later removed.

More recent prostheses using a different approach attempt to structurally resurface both of the articulating surfaces of the knee to provide a non-hinged type prosthesis. Such prostheses seek to remedy the failure of hinged devices, and involve two components which are respectively connected with the femur and tibia and held in engagement by the muscles and ligaments to produce a more lifelike situation.

The non-hinged knee prostheses must contend with the particulars of the human knee joint. The tibia is situated at the front (anterior) and inner (medial) side of the lower leg and, except for the femur, is the longest and largest bone in the human skeleton. It is prismoid in form, expanded above, where it enters into the knee joint. The head of the tibia is large and expanded on each side into two eminences called the tuberosities. The tops of these present two smooth concave surfaces which articulate within the knee with the condyles of the femur. The medial condyle is more prominent anteriorly and broader both in the anterior-posterior (front-rear) and transverse diameters than is the outside (lateral) condyle. Accordingly, the lateral top articular surface of the tibia is longer, deeper and narrower than the medial surface of the tibia so as to articulate with the lateral condyle. The medial surface is broader and more circular, concave from side to side, to articulate with the medial condyle. The anterior surfaces of the tuberosities are continuous with one another, forming a single large surface which is somewhat flattened. Posteriorly the tuberosities are separated from each other by a shallow depression for attachment of ligaments. The inner (medial) tuberosity presents posteriorly a deep transverse groove for the insertion of the posterior cruciate ligament (PCL).

In the past, tibial prostheses (commonly called baseplates because they fit beneath the condyles of the femur) were manufactured with total symmetry for use with both left and right knees which, as was discussed above, are not symmetrical. Although the symmetrical components were interchangeable between the right or left tibia, there were problems with the baseplate overhanging the lateral tibial bone surface or undersized on the medial tibial bone surface. The result was a compromise in the fit of the prosthesis. In response thereto, asymmetric tibial prostheses (baseplates) were developed to more closely approximate the natural tibial anatomy. The problem with such asymmetric tibial prostheses is that they require asymmetric, or knee specific removable tibial baseplate inserts (the concave bearing surface which actually contacts the femoral condyles) necessitating the need for a hospital to maintain an inventory of left and right knee specific inserts.

U.S. Pat. No. 4,963,152 provides a partial solution to the problems associated with symmetrical tibial prostheses. The patent discloses an asymmetrical tibial prosthesis whereby asymmetry is created by having the outer radius which describes the medial condyle slightly greater than the outer radius describing the lateral condyle. However, the baseplate is symmetrical about the medial-lateral centerline, allowing it to be used on either left or right tibia by rotating the baseplate 180° about the centerline. The insert, which is designed to mate with the baseplate, is also symmetrical about the medial-lateral centerline. The disadvantage of such a tibial prosthesis is that it must include an anterior as well as a posterior relief notch for the PCL in order to allow the baseplate to be reversed and thus usable on either the left or right knee. The "extra" notch, along with the symmetrical geometry of the baseplate about the medial-lateral centerline, does not provide the best coverage of the prosthesis upon the head of the tibia.

In order to provide the best coverage, the baseplate should be formed with only one notch for the PCL and thus cannot be symmetrical about either the medial-lateral centerline or the anterior-posterior centerline. However, such a baseplate would require a correspondingly asymmetrical insert under the teachings of the prior art.

Since these inserts may wear out and require replacement prior to the tibial baseplate, it becomes more costly from an administrative standpoint to maintain an inventory of both left and right knee inserts.

What is needed is a low cost symmetrical tibial insert that can be mass-produced so as to lower inventory and replacement costs and which is still usable in conjunction with an asymmetric tibial baseplate.

The object of the present invention is to provide a knee prosthesis having a tibial baseplate specific to the left or right tibia but allowing for the placement of an insert which is symmetrical about its anterior-posterior centerline and thus not left or right knee specific. The knee prosthesis also includes a femoral component having condyles for articulating with the condyle compartments of the symmetrical insert.

SUMMARY OF THE INVENTION

The present invention is for a knee replacement prosthesis comprising a baseplate having a medial end with a first arcuate outer perimeter and a lateral end with a second arcuate outer perimeter. The first arcuate outer perimeter has a radius of curvature greater than the radius of curvature associated with the second arcuate outer perimeter. The baseplate also has a means for receiving an insert on the upper surface of the baseplate, this means including arcuate peripheral ledges having equal radii circumscribed on the baseplate within the outer unequal radii. The insert has a medial condyle compartment and a lateral condyle compartment for articulating with femoral condyles of a femoral component. Each compartment has arcuate outer perimeters of equal radius for positioning in juxtaposition with the peripheral ledges of the baseplate.

The baseplate, insert and femoral component each include a notch between the medial end and the lateral end behind the medial-lateral centerline to allow for the PCL.

The baseplate is connectable to a human tibia and the femoral component is connectable to a human femur.

The baseplate further includes overhangs on the ledges along with at least one recessed lip for receiving a flexible latch attached to the underside of the insert for locking the insert to the baseplate. The baseplate also includes means for securing the baseplate to a resected surface of a patient's tibia. This means could include, if desired, a post which is received into a hole drilled into the head of the tibia whereby the post is bonded into the hole. Also, a hole within the tibial baseplate could be included, if desired, to allow for the baseplate to be attached to the resected head of the tibia with a bone screw.

The baseplate has a substantially elliptical circumference with the medial end having a radius different from the radius of the lateral end so that the baseplate precisely fits upon the resected surface of the tibia for the left and right knees. This eliminates an overhang of the baseplate beyond the circumference of the resected portion of the tibia resulting in a better fit of the tibial baseplate onto the tibia. The asymmetrical baseplate is configured to receive a symmetrical insert onto its upper surface. Thus, any one insert may be mounted to a left or right knee specific baseplate. The insert is configured with substantially similar medial and lateral condyle compartments for articulation with the femoral condyles of a femoral component when the total prosthesis is implanted within the knee.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF THE INVENTION

Figure 1:
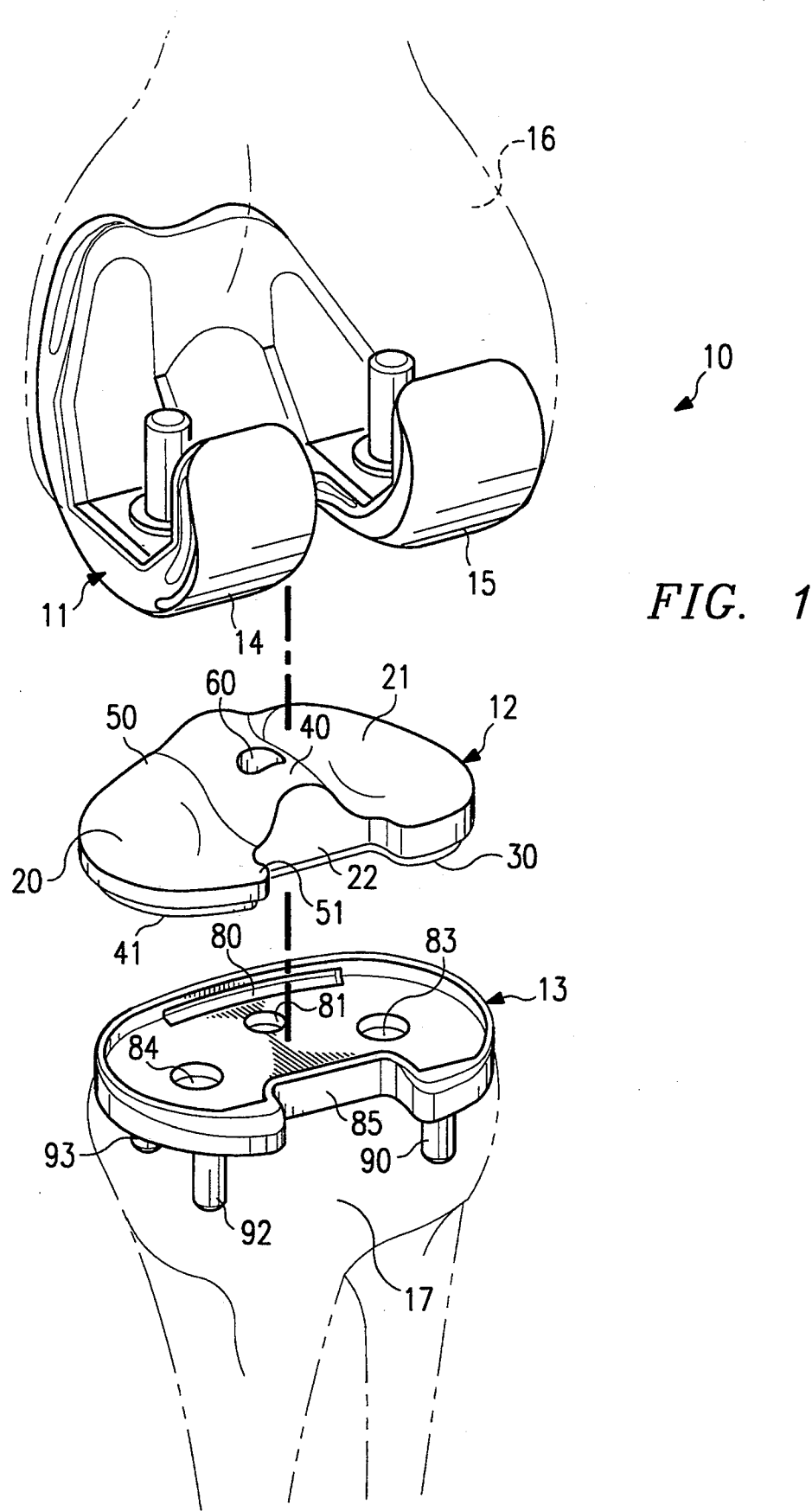
FIG. 1 illustrates an exploded view of a total knee replacement including a femoral component, a tibial baseplate and a corresponding tibial insert.

Referring to FIG. 1, there is shown knee replacement 10 observed from behind the right knee which generally consists of femoral component 11 having medial condyle 14 and lateral condyle 15. Femoral component 11 is attached to femur 16 by the surgeon and operates in conjunction with tibial baseplate 13 attached to tibia 17 and insert 12 mounted to baseplate 13.

Figure 2:
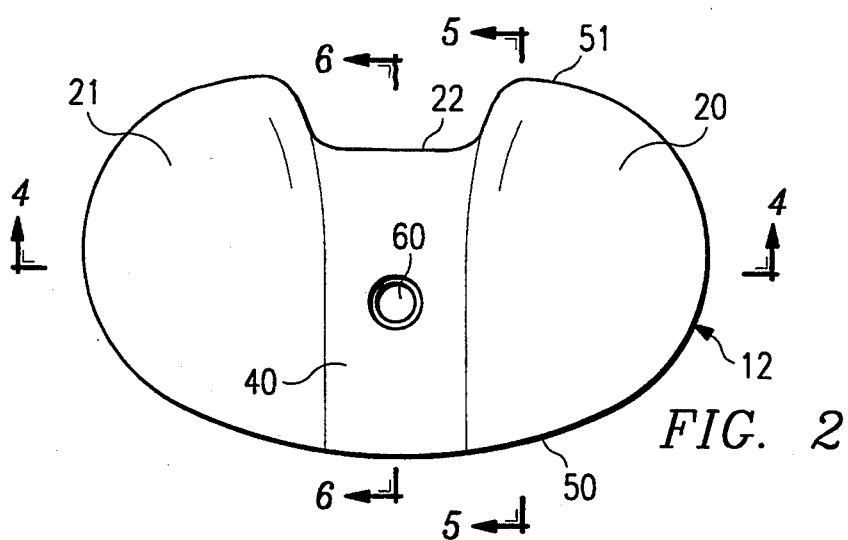
FIG. 2 illustrates a top view of the tibial insert.
Figure 3:
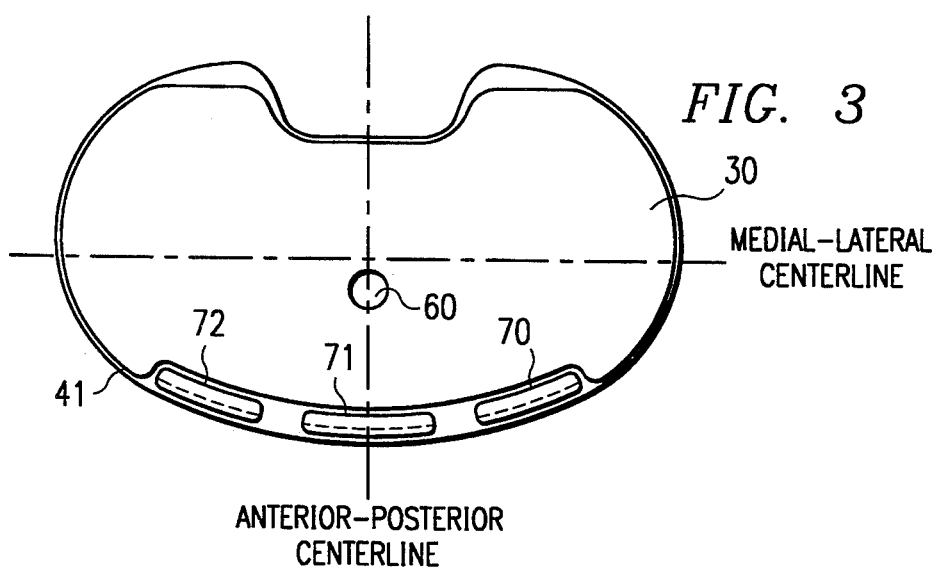
FIG. 3 illustrates a bottom view of the tibial insert.
Figure 4:
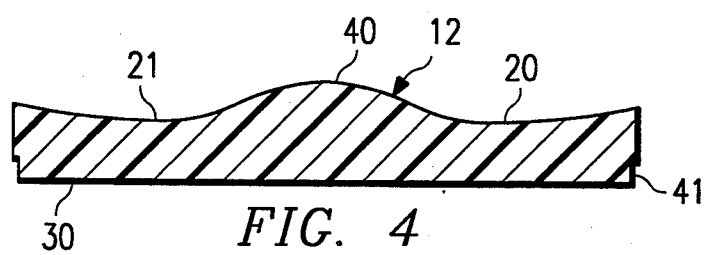
FIG. 4 illustrates a cross-sectional view of the tibial insert of FIG. 2 along section lines 4—4.

The superior insert surface, shown in FIGS. 1 and 2, is divided into three areas, medial condyle compartment 20, tibial eminence 40, and lateral condyle compartment 21. Condyle compartments 20 and 21 have substantially similar concave geometries and form the articulating surface for medial condyle 14 and lateral condyle 15 of femoral component 11. Since condyle compartments 20 and 21 are substantially identical and insert 12 is symmetrical about the anterior-posterior centerline (shown in FIG. 3), the terms "medial" and "lateral" are meaningful only after insert 12 is actually placed in a knee. Before placement of insert 12 into a knee, the two terms are completely interchangeable. This can be visualized if one were to imagine a left knee with a knee replacement positioned to the left of knee replacement 10. Such a left knee replacement would have a baseplate (similar to baseplate 13) (not shown) with its wider medial radius facing right while the wider medial radius of baseplate 13 faces left. The left and right baseplates are mirror images resulting in the medial end of each baseplate having a larger radius than the lateral end.

Figure 5:
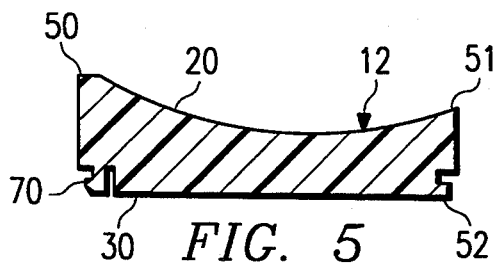
FIG. 5 illustrates a cross-sectional view of the tibial insert of FIG. 2 along section lines 5—5.

Refer next to FIG. 5, which is cross-section 5—5 of medial condyle compartment 20 of FIG. 2, and includes both an anterior lip 50 and a posterior lip 51 to limit anterior and posterior motion. Lateral condyle compartment 21 is similarly designed as medial condyle compartment 20. The contouring of condyle compartments 20 and 21 allows for normal internal and external rotation of the articulating couple and also allows for anterior-posterior and medial-lateral movement.

Referring to FIG. 2, the central portion of tibial eminence 40 supplies medial-lateral stability. Posterior portion 22 of insert 12 is notched to allow clearance for the PCL (not shown) when mated with tibial baseplate 13.

As shown in FIGS. 3–6, inferior insert surface 30 of insert 12 is flat, with indented edge 41 around its outer periphery. Edge 41 allows insert 12 to nest into the recess on the superior side of baseplate 13. Symmetrical insert 12 is locked into baseplate 13 by means of medial and lateral posterior "L" shaped protrusions 52 (shown in FIG. 5) which fit under overhangs 88 and 89 in baseplate 13, shown in FIG. 8. As illustrated in FIGS. 1, 3, 5–8 and 10, three anterior snap-locks 70, 71 and 72 are engaged into notch 80 on baseplate 13 with an inferiorly-directed force. Of course, any type of locking device could be used, including cement.

Figure 6:
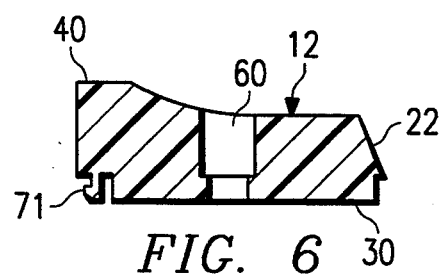
FIG. 6 illustrates a cross-sectional view of the tibial insert of FIG. 2 along section lines 6—6.
Figure 7:
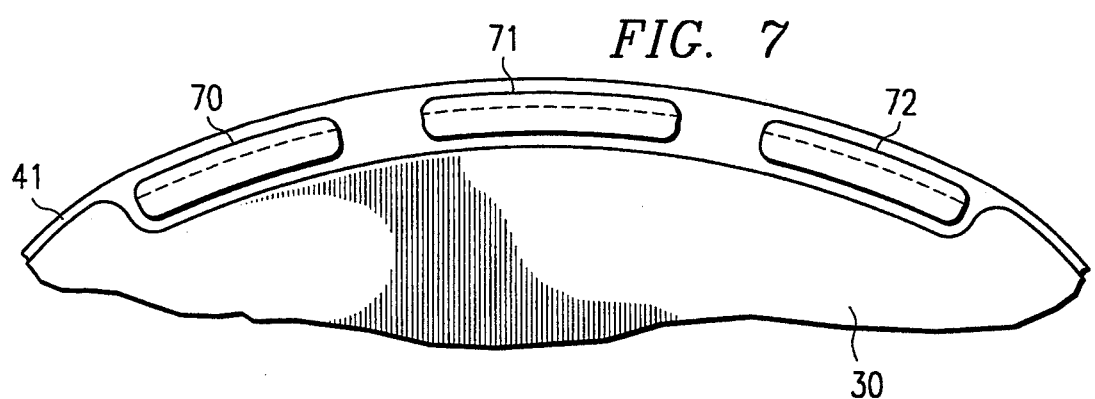
FIG. 7 illustrates a detail of a locking mechanism for securing the tibial insert to the tibial baseplate.

Referring to FIG. 6, passageway 60 is formed within tibial eminence 40 to allow insertion of a screw (not shown) to allow for an additional attachment of insert 12 to baseplate 13 whereby the screw is fastened to hole 81 in baseplate 13.

Insert 12 is preferably formed of an ultra-high molecular weight polyethylene (UHMWpe) in pure or fiber reinforced form produced by injection molding, compression molding or machining from bar or slab stock. Other biocompatible, low friction materials having a low wear rate, which can be shaped by molding or machining, could also be used.

Insert 12 (FIG. 2) is symmetrical about the anterior-posterior centerline (shown in FIG. 3) with only one notch 22 for the PCL. An advantage is ease of manufacture resulting in lower manufacturing and inventory costs for inserts that must be replaced due to wear and tear since insert 12 of the present invention is manufactured for use on both the right and left knees. In the present invention, the tolerances and geometries of medial and lateral condyles 20, 21 are substantially similar and are not dependent upon whether insert 12 is placed in the right or left knee. The manufacture of one common symmetrical insert allows the hospital to reduce its required inventory of inserts and relieves the physician of one more decision on whether or not the insert being placed in the tibial baseplate is the correct one for that particular knee.

Figure 8:
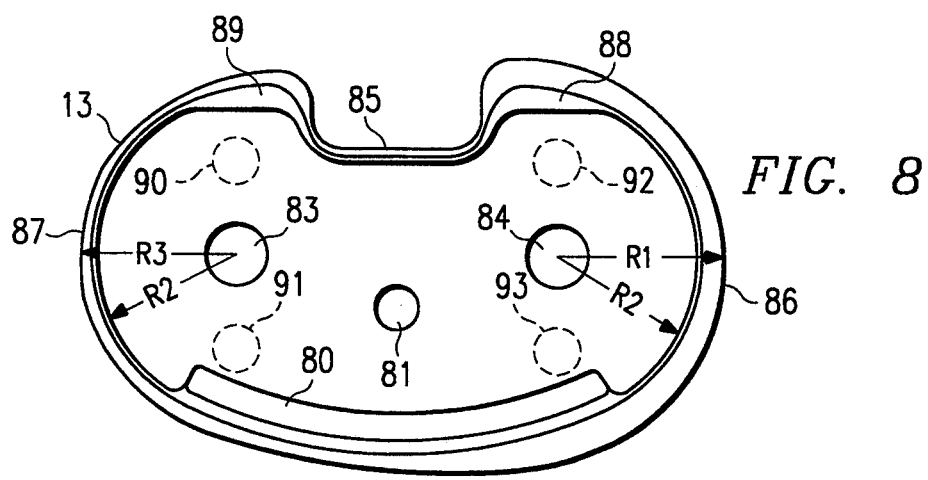
FIG. 8 illustrates a top view of a tibia baseplate for implant in a right knee.
Figure 9:
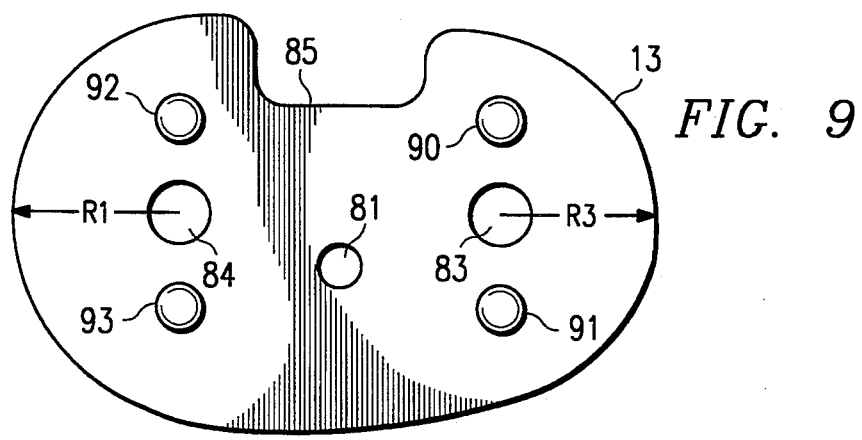
FIG. 9 illustrates a bottom view of the tibial baseplate for implant in a right knee.

Turning now to FIGS. 8 and 9, there is shown baseplate 13 which is implanted by the surgeon onto the resected head of tibia 17 (see FIG. 1). This implant can be attached in any one of a number of ways including gluing to tibia 17. One way would be for the surgeon to drill holes into the resected head of tibia 17 and to insert pegs 90, 91, 92 and 93 into the tibia holes as shown in FIG. 1. The surgeon could also, if desired, place screws through holes 83 and 84 of baseplate 13 into tibia 17. In any event, baseplate 13 is permanently mounted to tibia 17.

Figure 10:
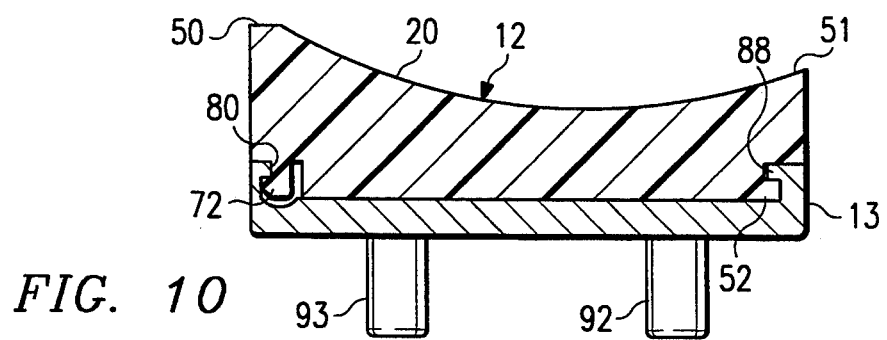
FIG. 10 illustrates a cross-sectional view of an assembled tibial baseplate and insert utilizing the cross-sectional view of the insert in FIG. 5.

As shown in FIG. 10, insert 12 is then snapped into baseplate 13 such that "L" shaped protrusions 52 shown in FIG. 5 of the posterior side of insert 12 slip into overhangs 88 and 89. Then snap-locks 70, 71 and 72 (flexible latches) of insert 12, which are located on the anterior side of insert 12, are snapped into notch 80 having a recessed lip, thereby locking insert 12 to baseplate 13.

It is important to note that insert 12, as has been discussed previously, is symmetrical about the anterior-posterior centerline such that the radius of curvature of the periphery of insert 12 measured from points within condyle 21 and condyle 20 is the same. Also note that as shown in FIG. 8, the radius of curvature of the medial circumference of outer periphery 86 of right knee baseplate 13 is R1, while the radius of curvature of the lateral circumference of outer periphery 87 of baseplate 13 is R3, and that R1 is greater than R3 so as to accommodate the physical structure of tibia 17 of the right knee, as discussed previously, such that medial radius of curvature R1 is greater than lateral radius of curvature R3. This allows baseplate 13 to fit coextensively on tibia 17 of the right knee so that there is no overhang or underhang, thereby more evenly distributing the load, thus reducing the occurrence of soft tissue rubbing on the overhang or the baseplate sinking into tibia if it is undersized. Note that the baseplate for the left knee would be the mirror image about the anterior-posterior centerline such that R3 would be longer than R1.

These differences in radius of curvature between R1 and R3 give rise to the fact that the surgeon must use a left baseplate and a right baseplate which are not symmetrical about the medial-lateral centerline and thus cannot be "reversed" thereby requiring two different baseplates. However, because the internal radii R2 of baseplate 13 for both left and right baseplate inserts are identical, insert 12 can be used in either the right or left baseplate. This then allows for only one kind of insert in inventory and allows for insert 12, as discussed above, to be symmetrical about its anterior-posterior axis.

As shown in FIGS. 8 and 9, the posterior section of baseplate 13 contains groove 85 for allowing the patient's PCL to pass therethrough.

Although the present invention and its advantages have been described in detail, it should be understood that various changes, substitutions and alterations can be made herein without departing from the spirit and scope of the invention as defined by the appended claims.

What is claimed is:

1. A bicondylar baseplate for a prosthesis, said baseplate adapted to couple with an insert, said insert having a medial condyle compartment and a lateral condyle compartment configured to articulate with femoral condyles, said baseplate comprising:

a medial end with a first arcuate outer perimeter having a first radius of curvature;

a lateral end with a second arcuate outer perimeter having a second radius of curvature, said first radius of curvature being greater than said second radius of curvature; and means adapted for receiving said insert on an upper surface of said baseplate, said means adapted for receiving comprising a recess formed within said baseplate, said recess having arcuate peripheral ledges internally circumscribed on said baseplate, said ledges having equal radii, wherein each compartment of said insert has arcuate outer perimeters of equal radius for positioning in juxtaposition with said arcuate peripheral ledges.

2. The baseplate in claim 1 further comprising:
a single notch between said medial end and said lateral end, said notch being behind a medial-lateral centerline.

3. The baseplate in claim 1 further comprising:
means for locking said insert to said baseplate, said locking means comprising overhangs on said ledges.

4. The baseplate in claim 3 wherein said locking means further includes at least one recessed lip for receiving a flexible latch attached to an underside of said insert.

5. The baseplate in claim 2 further comprising:
means for locking said insert to said baseplate, said locking means comprising overhangs positioned on either side of said notch.

6. The baseplate as recited in claim 1 further comprising:
means for securing said baseplate to a resected surface on a patient's tibia.

7. An implantable bicondylar plate, configured to mate with an end of a first bone, and configured to support a detachable insert, said insert having more than one condyle compartment for mating with more than one condyle at an end of a second bone, said condyle and said insert adapted for controlling articulation between said first and second bones when in mated relationship, said end of said first bone having an asymmetrical circumference with respect to medial and lateral edges of said end, said plate comprising:
means on a bottom surface thereof for attachment to said first bone, said bottom surface being an ellipse with differing circumferences with respect to medial and lateral ends of said bottom surface so as to mate coextensively with said end of said first bone; and
a top surface having a circumferential lip at a periphery thereof and extending upward from said top surface, said lip having a width which varies such that an outside periphery of said lip is asymmetrical and identical with the circumferences of said bottom surface and such that an inner periphery of said lip is symmetrical about both an anterior-posterior centerline and a medial-lateral centerline, said lip defining a support area for said insert.

8. The implantable plate in claim 7 further including a single notch between said medial and lateral ends located behind said medial-lateral centerline.

9. The implantable plate in claim 7 further comprising:
means for locking said insert to said plate.

10. The implantable plate in claim 9 wherein said locking means further includes at least one recessed lip configured to receive a flexible latch attached to an underside of said insert.

11. The implantable plate in claim 8 further comprising:
means for locking said insert to said plate, said locking means comprising overhangs positioned on either side of said notch.

12. The implantable plate as recited in claim 7 further comprising:
means for securing said plate to a resected surface on a patient's tibia.

13. A prosthesis comprising:
an insert; and
a biocondylar baseplate having:
a medial end with a first arcuate outer perimeter;
a lateral end with a second arcuate outer perimeter, said first arcuate outer perimeter having a first radius of curvature greater than a second radius of curvature associated with the second arcuate outer perimeter;
means for receiving said insert on an upper surface of said baseplate, said insert having a medial condyle compartment and a lateral condyle compartment for articulating with femoral condyles of a femoral component, said receiving means comprising arcuate peripheral ledges circumscribed on said baseplate, said ledges having equal radii, wherein each compartment of said insert has arcuate outer perimeters of equal radius for positioning in juxtaposition with said peripheral ledges.

14. The prosthesis in claim 13 wherein said baseplate, said insert and said femoral component each include:
a notch between the medial end and the lateral end, the notch being behind a medial-lateral centerline.

15. The prosthesis in claim 13 wherein said baseplate is configured to connect to a human tibia and wherein said femoral component is configured to connect to a human femur.

* * * * *